(12) United States Patent
Gaonkar et al.

(10) Patent No.: US 8,603,562 B2
(45) Date of Patent: Dec. 10, 2013

(54) COFFEE-DERIVED SURFACTANTS

(75) Inventors: Anilkumar G. Gaonkar, Buffalo Grove, IL (US); Bary Lyn Zeller, Glenview, IL (US); Allan Bradbury, Tuerkenfeld (GB); Anthony Wragg, Banbury (DE)

(73) Assignee: Intercontinental Great Brands LLC, East Hanover, NJ (US)

( * ) Notice: Subject to any disclaimer, the term of this patent is extended or adjusted under 35 U.S.C. 154(b) by 0 days.

(21) Appl. No.: 12/487,296

(22) Filed: Jun. 18, 2009

(65) Prior Publication Data

US 2009/0252850 A1 Oct. 8, 2009

Related U.S. Application Data

(63) Continuation of application No. 11/381,622, filed on May 4, 2006, now abandoned.

(51) Int. Cl.
  *A23F 5/00* (2006.01)
  *A23L 3/34* (2006.01)
  *C12P 19/04* (2006.01)

(52) U.S. Cl.
  USPC ............. 426/595; 426/594; 426/596; 426/45; 426/532; 435/101

(58) Field of Classification Search
  USPC ............. 426/595, 596, 594, 432, 45; 435/101
  See application file for complete search history.

(56) References Cited

U.S. PATENT DOCUMENTS

| | | | |
|---|---|---|---|
| 1,887,686 A | 11/1932 | Kennedy | |
| 2,893,990 A | 7/1959 | Hass | |
| 2,976,158 A * | 3/1961 | Morgan, Jr. et al. | 426/329 |
| 4,031,251 A * | 6/1977 | Margolis et al. | 426/387 |
| 4,820,543 A | 4/1989 | Osawa | |
| 4,835,002 A | 5/1989 | Wolf et al. | |
| 4,857,351 A | 8/1989 | Neilson et al. | |
| 5,006,648 A | 4/1991 | Van der Plank et al. | |
| 5,071,975 A | 12/1991 | Ver der Plank et al. | |
| 5,507,970 A | 4/1996 | Ishikawa et al. | |
| 5,576,044 A | 11/1996 | Chmiel et al. | |
| 5,741,538 A | 4/1998 | Stipp et al. | |
| 5,853,787 A | 12/1998 | Gurol | |
| 5,897,903 A | 4/1999 | Gerhard-Rieben et al. | |
| 5,922,385 A | 7/1999 | Stipp et al. | |
| 5,997,929 A * | 12/1999 | Heeb et al. | 426/433 |
| 6,291,006 B1 | 9/2001 | Butterbaugh et al. | |
| 6,444,253 B1 | 9/2002 | Conklin et al. | |
| 6,509,044 B2 | 1/2003 | Van Den Braak et al. | |
| 6,544,576 B2 | 4/2003 | Zeller et al. | |
| 6,572,905 B2 | 6/2003 | Zeller et al. | |
| 6,902,756 B2 | 6/2005 | Vlad | |
| 2002/0119236 A1 | 8/2002 | Yokoo et al. | |
| 2007/0274943 A1 | 11/2007 | Ishikubo et al. | |

FOREIGN PATENT DOCUMENTS

| | | |
|---|---|---|
| EP | 0 254 376 A1 | 1/1988 |
| JP | 53 104769 A | 9/1978 |
| JP | S61-124344 A | 6/1986 |
| JP | S63-66151 A | 3/1988 |
| JP | H10-66507 A | 3/1998 |
| JP | 2002-186425 A | 7/2002 |
| JP | 2003-116469 A | 4/2003 |
| JP | 2003-310212 A | 11/2003 |
| JP | 2005-089366 A | 4/2005 |

OTHER PUBLICATIONS

De Maria et al., Composition of Green Coffee Water-Soluble Fractions and Identifications of Volatiles Formed During Roasting. Food Chemistry vol. 55, No. 3 pp. 203-207 (1996).*
Das et al., Concentrated Emulsions, Studies on the influence of Continous-Phase Viscosity, Volume Fraction, Droplet Size, and Temperature on Emulsion Viscosity. Langmuir vol. 8, pp. 2427-2436 (1992).*
Residue—Webster's Dictionary (2011).*
Feuge, R.O., et al., "Preparation of Sucrose Esters by Interesterification" Journal of the American Oil Chemists' Society, AOCS Press, Champaign, IL, U.S., vol. 47, No. 2, Feb. 1970, pp. 56-60.
Ky, C.-L., et al., "Inheritance of Coffee Bean Sucrose Content in the Interspecific Cross Coffea Pseudozanguebariae X Coffea Liberica 'Dewevrei'" Plant Breeding, Paul Parey Scientific Publ., Berlin, Germany, vol. 119, No. 2, Apr. 2000, pp. 165-168.
Polat, T., et al., "Syntheses and Applications of Sucrose-Based Esters" Journal of Surfactants and Detergents, AOCS Press, Champaign, IL, U.S., vol. 4, No. 4, Oct. 2001, pp. 415-421.
Sivetz, M., et al., "Coffee and Its Influence on Consumers" AVI Publishing, Westport, 1979, pp. 568-574.
Hans Meyer and Alfred Eckert, The Fatty Oil and Wax of Coffee Beans, Monatshefte fuer Chemie, 1911, vol. 31, p. 1227 (Abstract, 1 page).
G. Urbaneja et al., Acid Hydrolysis and Carbohydrates Characterization of Coffee Pulp, Renewable Energy, vol. 9, Nos. 1-4, Sep.-Dec. 1996, pp. 1041-1044.
C. A. B. De Maria et al., Composition of green coffee fractions and their contribution to the volatile profile formed during roasting, Food Chemistry, vol. 50, No. 2, 1994, pp. 141-145.

\* cited by examiner

*Primary Examiner* — Rena Dye
*Assistant Examiner* — Assaf Zilbering
(74) *Attorney, Agent, or Firm* — Fitch, Even, Tabin & Flannery LLP

(57) ABSTRACT

Coffee-derived surfactants are provided by transesterification reactions of sugars and coffee oil. The coffee-derived surfactants are especially useful in the production of coffee oil emulsions for use with, or incorporation into, coffee products.

15 Claims, No Drawings

COFFEE-DERIVED SURFACTANTS

CROSS-REFERENCE TO RELATED APPLICATION

This application is a continuation of prior application Ser. No. 11/381,622, filed May 4, 2006, which is hereby incorporated herein by reference in its entirety.

FIELD OF THE INVENTION

This invention is directed to coffee-derived surfactants. More specifically, this invention is directed to coffee-derived surfactants prepared by transesterification reactions of sugars and coffee oil. The coffee-derived surfactants are especially useful in the production of coffee oil emulsions for use with, or incorporation into, coffee products.

BACKGROUND OF THE INVENTION

Soluble coffee, also referred to as instant coffee, is a convenient alternative to the more traditional roast and ground coffee (R&G). Instant coffees, however, often trade the robust flavor of the R&G bean for the convenience of quick preparation. Soluble coffee is typically made by extraction and thermal hydrolysis of roast and ground (R&G) coffee, followed by separation and drying of the extract. Often soluble coffees may have an imbalanced flavor and aroma due to the high degree of processing and associated losses. The high temperatures and pressures used in such processes often produce a lesser quality product as compared to traditional R&G coffee.

The inferior quality of the soluble coffees has been a long-standing problem. U.S. Pat. No. 5,576,044 (Nov. 19, 1996) provides an emulsion preconcentrate which contains hydrolyzed coffee oil and a coffee aroma. Coffee oil is hydrolyzed using, for example, alkaline hydrolysis using a conventional saponification process for fats and oils. The hydrolyzed oils generally have melting points greater than about 30° C. After adding the appropriate coffee aroma, the emulsion preconcentrate is added to soluble coffee particles (e.g., instant coffee). Once the coffee beverage is prepared, a "[s]mall amount of oil may appear on the surface, particularly if the hydrolyzed oil contains high levels of glycerides or the soluble coffee product contains unhydrolyzed oil. However, the amount of oil on the surface is well within acceptable ranges; for example equivalent to or less than that which would appear on the surface of roast and ground coffee."

U.S. Pat. No. 4,044,162 (Aug. 23, 1977) provides a method of improving the flavor and aroma of decaffeinated coffee by contacting green coffee with sucrose during the caffeine extraction process. The sucrose is reported to replace natural sucrose removed or destroyed during caffeine extraction.

U.S. Pat. No. 4,857,351 (Aug. 15, 1989) provides a method for treating coffee beans to improve flavor and aroma. One step in this process involves the treatment of partially roasted coffee beans with an alkaline solution at a temperature of about 4 to about 177° C.; a sugar can be added to the solution.

U.S. Pat. No. 6,291,006 (Sep. 18, 2001) provides a so-called dissolution agent that can be added to coffee and other beverages. The dissolution agent preferably includes lecithin, propylene glycol, ethoxylated mono and diglycerides, and a sucrose fatty acid ester, combined with maltodextrin and water to make a binder solution. The dissolution agent is added to the beverage product normally at a level of about 0.2 to about 0.33 percent.

There remains a need to provide an improved and more efficient method of producing soluble coffee that retains the robust coffee flavor and aroma similar to R&G coffee. There also remains a need to provide improved soluble coffee containing higher levels of coffee oils which, when prepared, do not form visible "oil-slicks."

SUMMARY OF THE INVENTION

This invention is directed to coffee-derived surfactants. More specifically, this invention is directed to coffee-derived surfactants prepared by transesterification reactions of sugars and coffee oil. The coffee-derived surfactants are especially useful in coffee products, including the production of coffee oil emulsions for use with, or incorporation into, coffee products.

In especially preferred embodiments, this invention is directed to highly effective emulsifiers produced from coffee materials to facilitate the formulation of emulsions and foams in coffee products (e.g., instant coffee) and to increase the incorporation of coffee oil into coffee products with reduced formation of so-called "oil slicks." The coffee-derived emulsifiers are prepared using a transesterification reaction to form sugar esters from coffee materials, especially coffee oils, and sugars (e.g., sucrose). In one embodiment, coffee oil, a non-reducing sugar (e.g., sucrose), and an alkaline catalyst (e.g., potassium carbonate) are reacted to provide a series of sugar monoesters. Sugars having reducing groups (e.g., mannose) can also be used in the present invention so long as the reducing groups are blocked (e.g., via alkylation of the reducing groups; see Example 7) prior to the transesterification reaction. For purposes of this invention, the term "sugar" is intended to include both non-reducing and reducing sugars; as noted, however, reducing sugars should be pre-modified by blocking the reducing groups prior to the transesterification reaction.

It is generally preferred that the raw materials used to prepare the coffee-derived surfactants are themselves derived from coffee materials. Thus, for example, sucrose used in the transesterification reaction can be obtained from coffee materials (e.g., extracted from green coffee). Green coffee or other coffee material can be ashed and hydrated to provide an alkaline residue which can be used in place of the alkaline catalyst (e.g., potassium carbonate).

The coffee-derived surfactants of this invention allow the incorporation of higher levels of coffee oils in instant type coffees and provide improved quality, reduced raw material costs, and reduced formation of "oil slicks" in instant type coffees.

DETAILED DESCRIPTION

The present invention provides coffee-derived surfactants by alkaline catalyzed transesterification reactions of sugars with coffee materials. The resulting coffee-derived surfactants are especially useful in the preparation of coffee oil emulsions which can then be used in preparation of coffee beverages (especially soluble coffee beverages). The resulting coffee oil emulsions are less likely to form oil slicks, as compared to other means of adding coffee oils, in instant type coffees. Incorporating more coffee oils in instant coffee products using the coffee-derived surfactants of this invention allows for improved flavor and aroma which more closely mimics the desired robust coffee flavor and aroma in R&G coffee. Moreover, since the surfactants are prepared from coffee materials, non-coffee surfactants are not added to the coffee products.

Coffee-derived surfactants are prepared by alkaline catalyzed transesterification reactions of sugars with coffee materials. Although not wishing to be limited by theory, it is thought that the coffee-derived surfactants produced in the present invention are largely a series of sugar monoesters formed during the transesterification reactions.

Suitable coffee materials for use in the present invention include, for example, roast and ground coffee, coffee oils, spent (i.e., partially extracted) coffee grounds or coffee oils, coffee aqueous extracts, green coffee bean extracts, and the like as well as mixtures thereof; the extracts or other coffee materials may be concentrated if desired. Preferably, the coffee material comprises coffee oils.

The sugars used in the present invention include monosaccharides (e.g., mannose, glucose, fructose, galactose and the like) and disaccharides (e.g., sucrose, lactose, maltose, trehalose, cellobiose, and the like) as well as mixtures thereof. Non-reducing sugars (e.g., sucrose, trehalose) can be used directly in the transesterification reaction. Sugars having reducing groups (i.e., reducing sugars such as mannose, glucose, fructose, galactose, lactose, maltose, and cellobiose) must have their reducing groups blocked (see, e.g., Example 7) prior to being subjected to the transesterification reactions. Preferred sugars are obtained from coffee materials such as roast and ground coffee, spent (i.e., partially extracted) coffee grounds, coffee aqueous extracts, green coffee bean extracts, and the like as well as mixtures thereof. Sugars derived from coffee materials, since they mainly consist of sucrose, can be used in the transesterification reaction without any blocking pretreatment or preconditioning. Especially preferred coffee materials from which sugars can be derived include spent coffee grounds.

Alkaline transesterification catalysts are used to form the desired transesterification products. Examples of such catalysts include $K_2CO_3$, KOH, NaOH, $Na_2CO_3$, $KHCO3$, $NaHCO_3$, and the like as well as mixtures thereof. Suitable catalysts also can be prepared from coffee materials. Thus, for example, coffee materials can be ashed (e.g., in a furnace at about 700° C. or higher) to produce a mineral residue containing various alkaline salts for use as the transesterification catalyst.

Generally, the transesterification reactions are carried out at about 130 to about 170° C. (preferably about 140 to about 160° C.) for about 4 to about 10 hours (preferably about 6 to about 8 hours) in a suitable solvent (e.g., dimethyl formamide and the like). The desired coffee-derived surfactants can be obtained from the reaction mixture by removing the solvent using conventional techniques (e.g., rotary evaporation).

In other embodiments, the coffee materials can be treated prior to, or during, the transesterification reaction to, for example, increase the level of free fatty acids in the coffee material. Thus, for example, coffee oil can be partially hydrolyzed at about 200 to about 300° C. for about 1 to about 4 hours to increase the free fatty acids content. Subsequent treatment of coffee oil with alkaline transesterification catalysts may, in addition to catalyzing the transesterification reactions, further increase the free fatty acid content. The free fatty acids are typically present as alkaline salts. Increasing the fatty acid content of coffee materials, such as by partial hydrolysis of coffee oil, may beneficially increase the dispersability or functionality of the transesterification reaction products of this invention.

Advantages and embodiments of this invention are further illustrated by the following examples but the particular materials and amounts thereof recited therein, as well as other conditions and details, should not be construed to unduly limit the invention. All parts, ratios, and percentages are by weight unless otherwise directed. All publications, including patents and published patent applications, are hereby incorporated by reference.

EXAMPLE 1

An aqueous extract (4.5 liters) of green coffee beans having about 10 percent dissolved solids was adjusted to pH 4.5 by addition of phosphoric acid. The extract was then passed through a column containing Amberlite XAD-1180 resin; the resulting eluate was then passed through a column containing polyamide PSC-6 resin. The resulting eluate was then passed through each of the columns a second time and then collected. This combination of columns is thought to preferentially remove acids, phenolic compounds, and proteins and proportionately increase the sucrose concentration. Water was added to complete the elution of the coffee extract from the columns and added to the collected elute. The eluate was freeze dried and then extracted with ethanol (6× by volume at 80° C.). Rotary evaporation of the ethanol extract gave 6 g of pale yellow powder. Gas chromatography analysis of the powder following trimethylsilylation indicated that sucrose was the major component and was present at a concentration of over 80 percent.

A mixture of sucrose fatty acid esters was produced by reacting the above-described sucrose preparation (3.5 g) with spent grounds coffee oil (6.0 g) in the presence of $K_2CO_3$ (1 g) catalyst in a polar solvent (25 ml dimethyl formamide) by heating for 8 hours in a 135° C. oil bath. $K_2CO_3$ was used to catalyze the transesterification reaction. $K_2CO_3$ is not surface-active and does not become chemically part of the sucrose fatty acid ester molecules produced. The reaction yielded a solidified brown mass (10.5 g) after rotary evaporation to remove dimethyl formamide. The brown residue was then extracted with diethyl ether; the insoluble portion (containing $K_2CO_3$) was discarded. The soluble portion, after removal of the diethyl ether by rotary evaporation, provided the solidified sucrose ester reaction product. Analysis using gas chromatography (GC) confirmed the formation of fatty acids corresponding to those present in coffee oil esters plus a series of peaks that eluted after sucrose. Analysis using liquid chromatography mass spectroscopy (LC-MS) identified these peaks as a series of sucrose monoesters.

The solidified reaction product containing the sucrose monoesters was combined with an equal part of water using a Turrax homogenizer; an equal amount of coffee oil was then added and the mixture emulsified using the Turrax homogenizer to produce a coffee oil emulsion. A drop of the resulting coffee oil emulsion placed on the surface of hot water. The drop dispersed without producing a visible surface slick. When a similar amount of coffee oil is added to the surface of hot water, an oil slick is observed.

EXAMPLE 2

Coffee oil (90 g), pressed from spent roasted coffee grounds obtained from a commercial soluble coffee process, was steam hydrolyzed by heating with water (10 g) at 250° C. for 2 hours in a sealed Parr bomb. Analysis indicated that the free fatty acid content of the partially hydrolyzed oil increased from 2.1 percent initially to 47.0 percent after treatment. The partially hydrolyzed coffee oil was used in Example 4.

EXAMPLE 3

A mixture of sucrose fatty acid esters was produced by reacting sucrose (13.7 g) with spent grounds coffee oil (12.0 g) in the presence of $K_2CO_3$ (4 g) catalyst by heating for 6 hours in dimethyl formamide at 140° C. $K_2CO_3$ was used to catalyze the transesterification reaction. $K_2CO_3$ is not surface-active and does not become chemically part of the sucrose fatty acid ester molecules produced. The reaction yielded a solidified brown mass (29.5 g). Analysis using gas chromatography (GC) confirmed the formation of fatty acids corresponding to those present in coffee oil esters plus a series of peaks that eluted after sucrose. Analysis using liquid chromatography mass spectroscopy (LC-MS) identified these peaks as a series of sucrose monoesters. It was estimated that about 5 percent of the sucrose was converted to sucrose monoesters under these unoptimized reaction conditions.

The solidified reaction product was first combined with an equal part of water using a Turrax homogenizer; to this mixture was added an equal part of coffee oil which was emulsified using the Turrax homogenizer. A drop of the resulting (50/50) emulsion placed on the surface of hot water. The drop dispersed without producing a visible surface slick.

For comparison purposes, sucrose (13.7 g) was combined with spent grounds coffee oil (12.0 g) in a beaker at room temperatures without an alkaline catalyst (e.g., $K_2CO_3$). The mixture was combined with an equal part of water using a Turrax homogenizer and a drop of the resulting (50/50) unstable coarse emulsion placed on the surface of hot water. A very apparent brown spotty oil slick resulted.

EXAMPLE 4

The process of Example 3 was essentially repeated using partially hydrolyzed spent grounds coffee oil (prepared in Example 2) in place of the spent grounds coffee oil. The reaction similarly produced a mixture of sucrose monoesters.

EXAMPLE 5

Green coffee beans (50 g) were ashed in a furnace at 800° C. for one hour to produce a mineral residue (4 g) containing alkaline potassium salts. The ash (4 g) was contacted with spent grounds coffee oil at 140° C. for 6 hours to produce free fatty acids as an alternative to the use of $K_2CO_3$ obtained from a non-coffee source. The ash can also be used as an alternative to $K_2CO_3$ obtained from a non-coffee source to catalyze the transesterification reaction to form the surfactant compositions of this invention. Thus, this material could be used, for example, to replace the $K_2CO_3$ catalyst of Example 1 to provide a surfactant composition prepared only from coffee-derived materials.

EXAMPLE 6

Ethanol was produced from an aqueous extract of green coffee beans by microbial fermentation using yeast from the *Saccharomyces* genus. Such ethanol, which is derived from coffee materials, can be used with sugars containing reducing groups to "block" (e.g., alkylation of the reducing groups). Such ethanol, for example, could be used as described in Example 7 to produce coffee-derived surfactants; if combined with the coffee-derived catalyst of Example 5, surfactant compositions prepared only from coffee-derived materials could be obtained.

EXAMPLE 7

A mixture of ethyl mannose fatty acid esters was produced by first reacting mannose (1.8 g) with ethanol (20 g) in the presence of Dowex cation-exchange resin in its $H^+$ form to catalyze production of ethyl mannose (2.1 g) and thereby blocking the reducing groups. Ethyl mannose (2 g) was then reacted with spent grounds coffee oil (3 g) in the presence of $K_2CO_3$ (1 g) by heating for 6 hours in a 140° C. oil bath. $K_2CO_3$ was used to catalyze the transesterification reaction. $K_2CO_3$ is not surface-active and does not become chemically part of the ethyl mannose fatty acid esters produced. The reaction yielded a solidified brown mass (6 g). Analysis using gas chromatography (GC) confirmed the formation of fatty acids corresponding to those present in coffee oil esters plus a series of peaks that eluted after mannose. Analysis using LC-MS identified these peaks as a series of ethyl mannose monoesters. It was estimated that 0.5 percent of the mannose was converted to ethyl mannose monoesters under these unoptimized reaction conditions. The solidified reaction product was combined with an equal part of water using a Turrax homogenizer and a drop of the resulting (50/50) emulsion placed on the surface of hot water. The drop dispersed without producing a visible surface slick.

For comparison purposes, mannose (1.8 g) was combined with spent grounds coffee oil (3.0 g) in a beaker at room temperatures without the use of an alkaline catalyst. The mixture was combined with an equal part of water using a PowerGen 700D mixer (Fisher Scientific) and a drop of the resulting (50/50) unstable coarse emulsion placed on the surface of hot water. A very apparent brown spotty oil slick resulted.

EXAMPLE 8

Roasted spent coffee grounds were contacted with water at high temperature using a commercial thermal hydrolysis process to prepare an aqueous coffee extract having a high concentration of mannose. The resulting extract could be used in the place of mannose in Example 7 to prepare mannose monoesters using only coffee-derived materials.

EXAMPLE 9

The sucrose monoester-containing reaction product (0.16 g) of Example 3 was combined with soybean oil (8.0 g), Maxwell House Instant Coffee powder (2.0 g), and water (7.84 g) and sheared using a PowerGen 700D mixer to produce a stable water-in-oil emulsion having average oil droplet size of 8 microns.

EXAMPLE 10

The sucrose monoester-containing reaction product (1.6 g) of Example 3 was combined with Maxwell House Instant Coffee powder (2.0 g), and water (230 g) in a 12 ounce cup and whipped using a PowerGen 700D mixer at 20,000 rpm for 30 seconds to produce a foamed coffee beverage having the appearance of espresso.

What is claimed is:
1. A soluble coffee comprising:
   a coffee-derived sugar-fatty acid ester composition obtained from a reaction of a portion of a first coffee material with a portion of a second coffee material; and
   a soluble coffee composition,
   wherein the coffee-derived sugar-fatty acid ester composition includes a sugar residue selected from the group consisting of monosaccharides, disaccharides and mixtures thereof derived from the first coffee material treated to increase the level of sugar and remove at least a portion of acids, phenolic compounds and proteins and a fatty acid residue derived from the second coffee mate- rial, the coffee-derived sugar-fatty acid ester composition further including unreacted coffee material and coffee material by-products in addition to sugar-fatty acid esters, the sugar residue including sugar selected from the group consisting of mannose, glucose, fructose, galactose, cellobiose and mixtures thereof, wherein the first coffee material is selected from the group consisting of roast and ground coffee, spent coffee ground, coffee aqueous extract, green coffee bean extract, and mixtures thereof, and wherein the second coffee material is selected from the group consisting of roast and ground coffee, coffee oil, spent coffee ground, spent coffee oil, coffee aqueous extract, green coffee bean extract, and mixtures thereof.

2. The soluble coffee of claim 1, wherein the second coffee material is coffee oil.

3. The soluble coffee of claim 1, wherein the sugar residue includes mannose.

4. The soluble coffee of claim 1, wherein the sugar-fatty acid ester is a surfactant that is the transesterification product of a sugar derived from the first coffee material with the second coffee material using an alkaline transesterification catalyst derived from a third coffee material.

5. The soluble coffee of claim 4, wherein the first, second and third coffee materials are the same.

6. The soluble coffee of claim 4, wherein the third coffee material is an ashed coffee material.

7. The soluble coffee of claim 1, wherein the first coffee material is treated to contain at least 80% sugars.

8. A coffee-derived surfactant comprising:
a sugar-fatty acid ester composition which includes a transesterification product of a sugar derived from a first coffee material with a coffee oil using an ashed coffee material as an alkaline catalyst,
wherein the sugar-fatty acid ester composition includes a sugar residue and a fatty acid source, the sugar residue selected from the group consisting of monosaccharides, disaccharides and mixtures thereof derived from the first coffee material and the fatty acid source being the coffee oil such that the sugar-fatty acid ester does not include any non-coffee derived materials, wherein the sugar-fatty acid composition further includes unreacted coffee material and coffee material by-products and wherein the sugar residue includes sugar selected from the group consisting of mannose, glucose, fructose, galactose, cellobiose and mixtures thereof.

9. The coffee-derived surfactant of claim 8, wherein the first coffee material is selected from the group consisting of roast and ground coffee, spent coffee ground, coffee aqueous extract, green coffee bean extract, and mixtures thereof.

10. The coffee-derived surfactant of claim 8, wherein the sugar residue includes mannose.

11. The coffee-derived surfactant of claim 8, wherein the coffee-derived surfactant is added to water to create a stable oil-in-water emulsion.

12. The coffee-derived surfactant of claim 11, wherein the oil-in-water emulsion has an average droplet size of 8 microns.

13. The coffee-derived surfactant of claim 8 in combination with a soluble coffee material.

14. A soluble coffee consisting essentially of:
a coffee-derived sugar-fatty acid ester composition obtained from a reaction of a portion of a first coffee material with a portion of a second coffee material; and
a soluble coffee composition,
wherein the coffee-derived sugar-fatty acid ester composition includes a sugar residue selected from the group consisting of monosaccharides, disaccharides and mixtures thereof derived from the first coffee material treated to increase the level of sugar and remove at least a portion of acids, phenolic compounds and proteins and a fatty acid residue derived from the second coffee material such that the coffee-derived sugar-fatty acid ester composition does not include any non-coffee derived materials, including unreacted coffee materials and coffee material by-products in addition to sugar-fatty acid esters, wherein the sugar residue includes sugar selected from the group consisting of mannose, glucose, fructose, galactose, cellobiose and mixtures thereof.

15. The soluble coffee composition of claim 14 wherein the sugar fatty-acid ester composition includes mannose monoesters prepared from spent coffee grounds using thermal hydrolysis, unreacted spent coffee grounds and by-products of thermal hydrolysis of spent coffee grounds.

* * * * *